March 13, 1934. C. B. FOX Plant Pat. 89
PENDULOUS JUNIPERUS SCOPULORUM
Filed Jan. 6, 1931
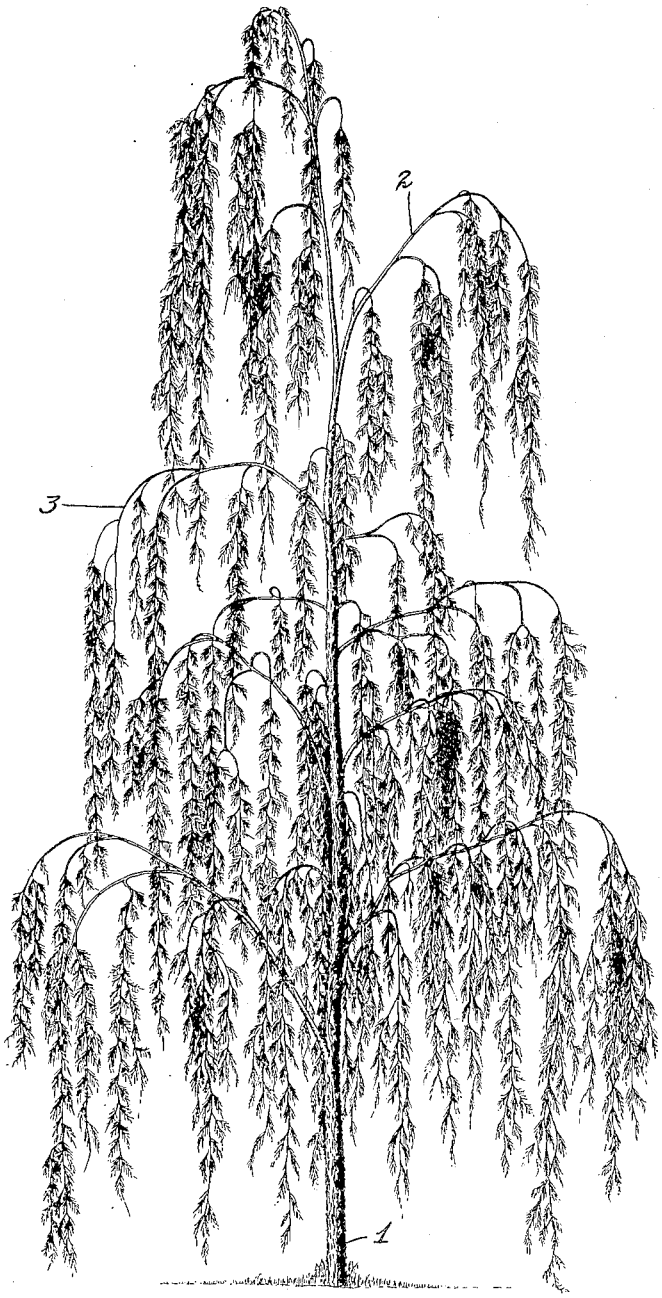
C. Burton Fox
INVENTOR
BY F. K. Bryant,
ATTORNEY Patented Mar. 13, 1934 Plant Pat. 89

UNITED STATES PATENT OFFICE

89

PENDULOUS JUNIPERUS SCOPULORUM

Carl Burton Fox, Tulsa, Okla., assignor of one-fourth to George X. Frey, Santa Fe, N. Mex.

Application January 6, 1931, Serial No. 507,034

1 Claim. (Cl. 47—59)

This discovery relates to a new and distinct pendulous variety of the species *Juniperus scopulorum* which includes the distinguishing characteristics hereinafter pointed out.

In the accompanying illustration the figure is a side elevational view, or perspective of a growing tree showing characteristic features of the new variety.

This plant was discovered by me and is believed to be the product of a mutuant (a mutation), or an extreme variation from the usual types of the family of *Juniperus scopulorum* or Rocky Mountain silver cedar.

The trunk 1 is upright and slightly crooked. The branches 2 are somewhat symmetrically arranged around the trunk extending out therefrom and usually slightly upward at an angle of approximately thirty or forty degrees from a horizontal line, but curving downward toward ends forming many lateral branches 3 which are long, extremely slender and extremely pendulous. These extremely slender pendulous branches vary but slightly in their diameter along their entire length, many of them measuring from one-eighth to one-fourth inch in diameter where joining onto the trunk or larger branches and graduating down to their tips along a length of from three to six feet, thereby showing little or no difference in their diameter along their entire length.

The difference between this juniper and any other juniper with drooping branches is that this juniper has branches that are extremely slender and pendulous and hang directly downward or vertical, their full length, while heretofore such plants have had the tips of the branches or foliage bending slightly downward. The branches of this *Juniperus scopulorum* are extremely pendulous hanging as so many pendulums.

The reproduction or propagation of this plant has been by asexual methods and has been propagated by me by grafting scions onto understock and by striking and rooting cuttings.

There are several new trees of this variety now growing at my experimental grounds.

The drawing illustrates my new tree in erect position with the branches thereof in natural poise.

Having described the discovery, what is claimed is:

A *Juniperus scopulorum* tree as herein shown and described, characterized by the extremely slender pendulous branches.

C. BURTON FOX.